United States Patent [19]

Parker

[11] Patent Number: 5,743,896
[45] Date of Patent: Apr. 28, 1998

[54] SANITARY NAPKIN HAVING A PROTRUSION INSERTABLE INTO THE POSTERIOR RUGAE OF THE BUTTOCKS

[76] Inventor: Beverly Marie Parker, 4414 Townsend, Detroit, Mich. 48214

[21] Appl. No.: 568,651

[22] Filed: Dec. 7, 1995

[51] Int. Cl.⁶ .......................... A61F 13/15; A61F 13/20
[52] U.S. Cl. ............................. 604/385.1; 604/387
[58] Field of Search ................ 604/358, 385.1, 604/387, 378, 368, 386

[56] References Cited

U.S. PATENT DOCUMENTS

| | | | |
|---|---|---|---|
| 2,331,355 | 10/1943 | Strongson | 604/385.1 |
| 3,183,909 | 5/1965 | Roehr | 604/385.1 |
| 4,046,147 | 9/1977 | Berg | 604/387 |
| 4,820,295 | 4/1989 | Chapes et al. | 604/385.1 |
| 4,846,824 | 7/1989 | Lessen et al. | 604/385.1 |
| 5,057,096 | 10/1991 | Feglione | 604/385.1 |
| 5,290,262 | 3/1994 | Vukos et al. | 604/385.1 |
| 5,324,278 | 6/1994 | Visscher et al. | 604/378 |
| 5,383,868 | 1/1995 | Hyun | 604/385.1 |
| 5,383,869 | 1/1995 | Osborn, III | 604/385.1 |
| 5,387,210 | 2/1995 | Murakami | 604/396 |
| 5,507,735 | 4/1996 | Von Iten et al. | 604/387 |

*Primary Examiner*—Mark Polutta
*Attorney, Agent, or Firm*—Joseph N. Breaux

[57] ABSTRACT

An improved sanitary napkin including a first padding section having a channel that is formed along the longitudinal axis thereof; a second padding section sized in a manner such that an extending portion of the second padding section extends away from the second surface of the first padding section when a portion of the second padding section is disposed within the channel; a screen barrier having a screen channel formed within the screen barrier at a location allowing the extending portion of the second padding section to be entirely disposed within the screen channel when the screen barrier is placed over the surface of the first padding section; and a liquid impermeable barrier section entirely covering the back surface of the first padding member and extending over the perimeter of the screen barrier and adhesively secured to the exterior surface of the screen barrier in a manner to seal the first and second padding sections between the liquid impermeable section and the screen barrier. The exterior surface of the liquid impermeable barrier that covers the first padding surface has a layer of adhesive disposed thereon that is covered with a removable cover member.

2 Claims, 1 Drawing Sheet

SANITARY NAPKIN HAVING A PROTRUSION INSERTABLE INTO THE POSTERIOR RUGAE OF THE BUTTOCKS

TECHNICAL FIELD

The present invention relates to sanitary napkins and more particularly to an improved sanitary napkin having a protruding, absorption pad for simultaneously channeling heavy menstrual fluid discharges into a primary absorption pad and maintaining the sanitary napkin in the correct position during use.

BACKGROUND ART

In use, sanitary napkins are generally placed in contact with the labia majora at a location sufficiently proximate the menstrual flow site to capture and hold menstrual fluid as the menstrual fluid is discharged. During high menstrual fluid flow periods or when twisting and/or folding of the sanitary napkin has occurred, leakage of menstrual fluid can occur resulting in embarrassment and stained garments. This twisting and/or folding typically occurs in the portion of the sanitary napkin positioned adjacent the buttocks of the wearer and covering a portion of the posterior rugae (the gap between the left and right buttocks). Leakage generally occurs through the gap formed between the pad and the skin surface of the posterior rugae.

It would be a benefit, therefore, to have a sanitary napkin that included an absorbent pad section extending from the conventional planar, absorbent pad member of the napkin that was shaped to fill the gap formed between the conventional planar, absorbent pad member and the skin surface defining the posterior rugae gap during use and, thereby, prevent undesirable leaks. It would also be a benefit to have a sanitary napkin that included a padding structure that reduced the amount of twisting and shifting of the sanitary napkin during use.

GENERAL SUMMARY DISCUSSION OF INVENTION

It is thus an object of the invention to provide a improved sanitary napkin that includes an absorbent pad section extending from the conventional planar, absorbent pad member of the napkin that is shaped to fill the gap formed between the conventional planar, absorbent pad member and the skin surface defining the posterior rugae gap during use.

It is a further object of the invention to provide a improved sanitary napkin that includes a padding structure that fits within a portion of the posterior rugae between the buttocks of a wearer to reduce the amount of twisting and shifting of the sanitary napkin during use.

It is a still further object of the invention to provide a improved sanitary napkin that achieves both of the above objects in combination.

It is a still further object of the invention to provide a improved sanitary napkin that accomplishes the above objects with the same physical structures.

Accordingly, an improved sanitary napkin is provided. The improved sanitary napkin includes a first padding section having a first section perimeter and a first section length, the first padding section including a first substantially planar surface and a second substantially planar surface, the second surface having a channel of a first channel depth, a first channel width, and a first channel length measuring at least one-half the first section length of the first padding section, that is formed along the longitudinal axis of the first padding section extending from a rear portion of the first padding section past at least a center point of the first padding section; a second padding section having a second section length that is less than the first channel length, a second section width that is less than the first channel width, and a thickness at least twice as great as the first channel depth in a manner such that an extending portion of the second padding section extends away from the second surface of the first padding section; a screen barrier having a screen perimeter corresponding to the perimeter of the first padding section and a screen channel formed within the screen barrier at a location allowing the extending portion of the second padding section to be entirely disposed within the screen channel when the screen barrier is placed over the second surface of the first padding section; and a liquid impermeable barrier section entirely covering the first surface of the first padding member and extending over the first section perimeter the screen barrier perimeter and adhesively secured to the exterior surface of the screen barrier in a manner to seal the first and second padding sections between the liquid impermeable section and the screen barrier, the exterior surface of the liquid impermeable barrier covering the first padding surface having a layer of adhesive disposed thereon covered with a removable cover member.

BRIEF DESCRIPTION OF DRAWINGS

For a further understanding of the nature and objects of the present invention, reference should be had to the following detailed description, taken in conjunction with the accompanying drawings, in which like elements are given the same or analogous reference numbers and wherein.

EXEMPLARY MODE FOR CARRYING OUT THE INVENTION

Figure 1:
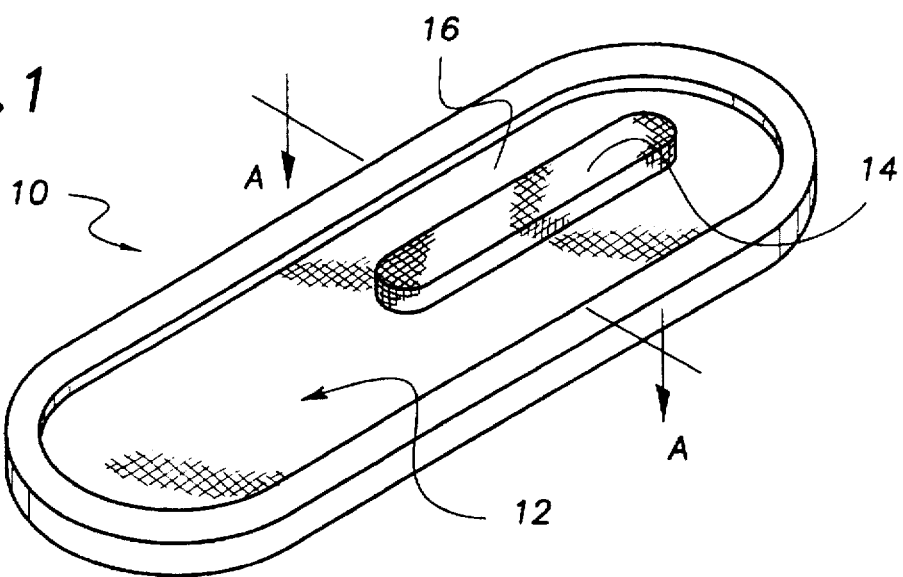
FIG. 1 is a perspective view of an exemplary embodiment of the improved sanitary napkin of the present invention showing the body contacting side including a section of padding extending outwardly from the conventional planar padding section.
Figure 2:
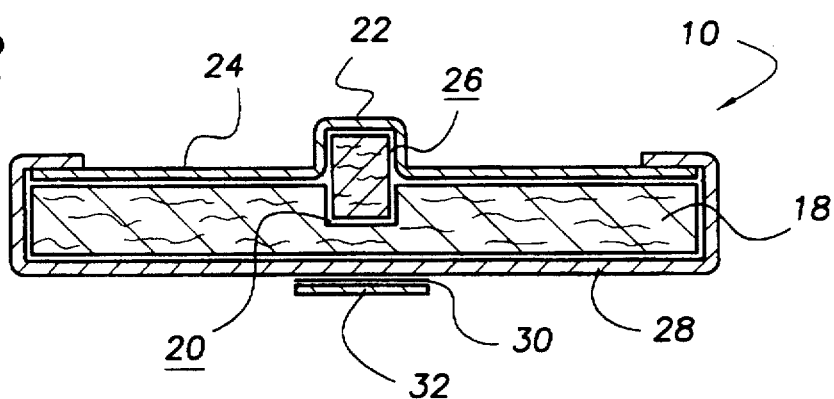
FIG. 2 is a cross-sectional view of the embodiment of the improved sanitary napkin along the line A—A of FIG. 1 showing the first padding section including the first channel, the second padding section, the screen barrier including the screen channel, the liquid impermeable section, and the attachment between the screen barrier and the liquid impermeable section.

FIG. 1 is a perspective view showing an exemplary embodiment of the improved sanitary napkin of the present invention generally designated by the numeral 10. Sanitary napkin 10 includes a body contacting side, generally designated by the numeral 12, including a protruding portion 14 that houses a section of padding (shown in FIG. 2) and extends outwardly from a conventional planar section 16. With reference to FIG. 2, a cross-sectional view of sanitary sanitary napkin 10 along the line A—A of FIG. 1, sanitary napkin 10 includes a first padding section 18 including a first channel 20; a second padding section 22, a screen barrier 24 including a screen channel 26, a liquid impermeable member 28, an adhesive layer 30, and a peel off cover member 32.

First padding section 18 is a section of conventional, absorbent, sanitary napkin padding and includes a substantially rectangular central section and two half-circular opposed end sections. First padding section 18 is about five inches long, two inches wide, and about three-quarters (¾") of an inch thick. The first channel 20 has a substantially rectangularly shaped cross section and is formed into one of the substantially planar surfaces. First channel 20 is about two and three-quarters (2¾") inches long, one-half (½") inch wide, and about two-fifths (⅖") inch deep. The first end of first channel 20 is positioned about one-half (½") inch from the rear end of first padding section 18 and extends along the longitudinal axis past the center point thereof.

Second padding section 22 is a section of conventional, absorbent, sanitary napkin padding having a substantially rectangular cross-section and is about two and three-quarters (2¾") inches long, one-half (½") inch wide, and about one (1") inch thick. Second padding section 22 has a portion inserted within first channel 20 and a portion that extends away from first padding section 18.

Screen barrier 24 is a section of open weave plastic screening that has a perimeter that corresponds to the perimeter of first padding section 18. Screen barrier 24 operates in the conventional manner to form a liquid permeable barrier between the user and the absorbent padding sections 18,22. Screen channel 26 is formed into screen barrier 24 at a location that allows the extending portion of second padding section 22 to be entirely disposed within screen channel 26 when screen barrier 24 is placed over first padding section 18.

Figure 3:
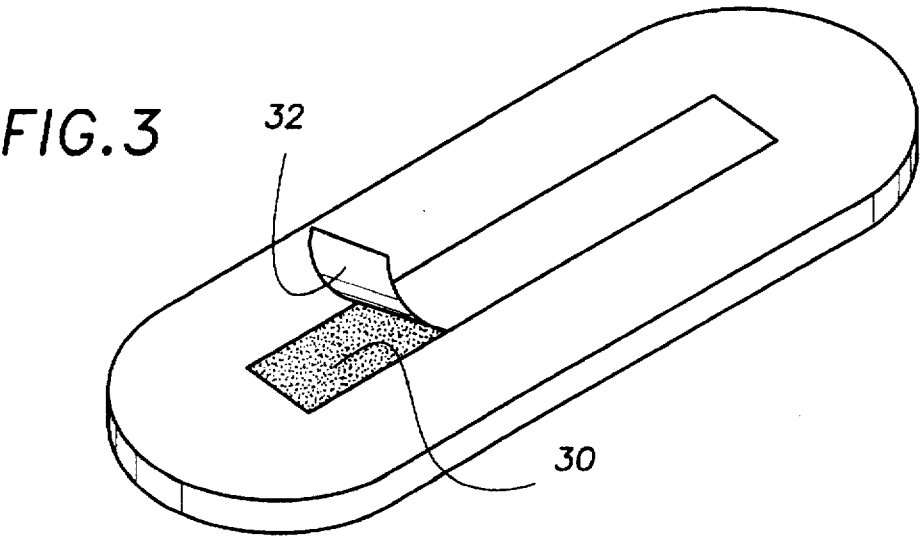
FIG. 3 is a perspective view of the sanitary napkin of FIG. 1 from the undergarment contacting side including the layer of adhesive utilized for securing the napkin to the inside of an undergarment during use.

Liquid impermeable barrier section 28 is constructed from lightweight plastic sheeting and entirely covers one side surface and the side edges of first padding section 18 and extends over the perimeter edge of screen barrier 24. Impermeable barrier section 28 is adhesively secured to screen barrier 24 in a manner to seal first and second padding sections 18, 22 between impermeable barrier section 28 and screen barrier 24. A layer of fabric adhering adhesive 30 is deposited along the exterior surface of impermeable barrier section 28 along substantially the entire length thereof and a removable cover member 32 positioned onto adhesive layer 30. With reference to FIG. 3, removable cover member 32 is shown partially peeled away from adhesive layer 30.

Use of improved sanitary napkin 10 is now described with general reference to FIGS. 1–3. Napkin 10 is secured to an undergarment by removing cover member 32 and positioning adhesive layer 30 onto an inside surface of the undergarment in a manner such that when the undergarment is donned, protruding portion 14 is positioned within the posterior rugae of the wearer. The remaining portions of napkin 10 are positioned in the same fashion as a conventional sanitary napkin. By positioning protruding portion 14 within the posterior rugae of the wearer a potential leakage point is plugged and the additional positioning support reduces twisting and folding of the napkin during normal wear.

It can be seen from the preceding description that an improved sanitary napkin has been provided that includes an absorbent pad section extending from the conventional planar, absorbent pad member of the napkin that is shaped to fill the gap formed between the conventional planar, absorbent pad member and the skin surface defining the posterior rugae gap during use, that includes a padding structure that fits within a portion of the posterior rugae between the buttocks of a wearer to reduce the amount of twisting and shifting of the sanitary napkin during use, and that achieves both of the above objects in combination with the same physical structures.

It is noted that the embodiment of the improved sanitary napkin described herein in detail for exemplary purposes is of course subject to many different variations in structure, design, application and methodology. Because many varying and different embodiments may be made within the scope of the inventive concept(s) herein taught, and because many modifications may be made in the embodiment herein detailed in accordance with the descriptive requirements of the law, it is to be understood that the details herein are to be interpreted as illustrative and not in a limiting sense.

What is claimed is:

1. A sanitary napkin having a protrusion insertable into the posterior rugae between the buttocks of a wearer, said sanitary napkin comprising:

an absorbent padding member including a protruding pad portion that extends from a substantially planar side thereof, said protruding pad portion extending from said planar side along a length of said absorbent padding member equal to at least one-half the length of said absorbent pad member, said absorbent padding member including a first padding section having a first section perimeter and a first section length, said first padding section including a first substantially planar surface and a second substantially planar surface, said second surface having a channel of a first channel depth of two-fifths of an inch, a first channel width of one-half, and a first channel length measuring at least one-half said first section length of said first padding section and a linear length of two and three-quarters inches, that is formed along a longitudinal axis of said first padding section extending from a rear portion of said first padding section beginning one-half inch from a rear end of said first padding section past at least a center point of said first padding section, and a second padding section having a second section length that is less than said first channel length, a second section width that is less than said first channel width, and a thickness at least twice as great as said first channel depth in a manner such that an extending portion of said second padding section extends away from said second surface of said first padding section and forms said protruding portion;

a screen barrier including a protruding screen portion having a screen channel formed therein, said screen barrier having a screen perimeter corresponding to said perimeter of said first padding section and a screen channel formed within said screen barrier at a location allowing extending portion of said second padding section to be entirely disposed within said screen channel when said screen barrier is placed over said second surface of said first padding section; and a liquid impermeable member secured around a perimeter of said screen barrier in a manner such that said absorbent padding member is secured within a chamber formed between said screen barrier and said liquid impermeable member when said protruding pad portion is disposed within said screen channel, an exterior surface of said liquid impermeable barrier that covers said first padding surface having a layer of adhesive disposed thereon covered with a removable cover member.

2. A method of maintaining a sanitary napkin in position during use comprising the steps of:

I) providing a sanitary napkin having a protrusion insertable into the posterior rugae between the buttocks of a wearer, said sanitary napkin comprising:

an absorbent padding member including a protruding pad portion that extends from a substantially planar side thereof, said protruding pad portion extending from said planar side along a length of said absorbent padding member equal to at least one-half the length of said absorbent pad member, said absorbent padding member including a first padding section having a first section perimeter and a first section length, said first padding section including a first substantially planar surface and a second substantially planar surface, said second surface having a channel of a first channel depth of two-fifths of an inch, a first channel width of one-half inch, and a first channel length measuring at least one-half said first section length of said first padding section and a linear length of two and three-quarters inches, that is formed along a longitudinal axis of said first padding section extending from a rear portion of said first padding section beginning one-half inch from a rear end of said first padding section past at least a center point of said first padding section, and a second padding section having a second section length that is less than said first channel length, a second section width that is less than said first channel width, and a thickness at least twice as great as said first channel depth in a manner such that an extending portion of said second padding section extends away from said second surface of said first padding section and forms said protruding portion;

a screen barrier including a protruding screen portion having a screen channel formed therein, said screen barrier having a screen perimeter corresponding to said perimeter of said first padding section and a screen channel formed within said screen barrier at a location allowing said extending portion of said second padding section to be entirely disposed within said screen channel when said screen barrier is placed over said second surface of said first padding section; and a liquid impermeable member secured around a perimeter of said screen barrier in a manner such that said absorbent padding member is secured within a chamber formed between said screen barrier and said liquid impermeable member when said protruding pad portion is disposed within said screen channel, an exterior surface of said liquid impermeable barrier that covers said first padding surface having a layer of adhesive disposed thereon covered with a removable cover member; and ii) positioning said protruding pad portion into the posterior rugae of the wearer.

* * * * *